United States Patent
Feyt et al.

(10) Patent No.: US 7,691,971 B2
(45) Date of Patent: Apr. 6, 2010

(54) PROTEIN NMB1125 AND USE THEREOF IN PHARMACEUTICAL FORMULATIONS

(75) Inventors: Rolando Pajon Feyt, La Habana (CU);
Enrique Guillen Nieto Gerardo, Ciudad de la Habana (CU); Gretel Sardinas Garcia, Ciudad de la Habana (CU); Nunez Lazaro Hiram Betancourt, Ciudad de la Habana (CU); Serra Lila Rosa Castellanos, Ciudad de la Habana (CU); Negrin Yasser Perera, La Habana (CU); Diaz Darien Garcia, Ciudad de la Habana (CU); Perez Olivia Niebla, Cindad de la Habana (CU); Menendez Evelin Caballero, Ciudad de la Habana (CU); Blanco Sonia Gonzalez, Cindad Habana (CU)

(73) Assignee: Centro Ingenieria Genetica Y Biotecnologia, Cuidad de la Habana (CU)

( * ) Notice: Subject to any disclaimer, the term of this patent is extended or adjusted under 35 U.S.C. 154(b) by 169 days.

(21) Appl. No.: 10/580,508

(22) PCT Filed: Dec. 2, 2004

(86) PCT No.: PCT/CU2004/000015

§ 371 (c)(1),
(2), (4) Date: Oct. 31, 2006

(87) PCT Pub. No.: WO2005/054281

PCT Pub. Date: Jun. 16, 2005

(65) Prior Publication Data

US 2007/0218000 A1  Sep. 20, 2007

(30) Foreign Application Priority Data

Dec. 3, 2003  (CU) ............................ CU2003/0285

(51) Int. Cl.
*C07K 14/00* (2006.01)
*C07K 17/00* (2006.01)

(52) U.S. Cl. .................................................... 530/350
(58) Field of Classification Search ........................ None
See application file for complete search history.

(56) References Cited

U.S. PATENT DOCUMENTS 6,146,635 A  11/2000  Cano et al.

FOREIGN PATENT DOCUMENTS

WO  WO 99/57280  * 11/1999
WO  WO 99/57280 A2  * 11/1999
WO  WO/0066791  11/2000

OTHER PUBLICATIONS

Marrazzo, Jeanne M, 7 Infectious Disease, III Infections Due to Neisseria, ACP Medicine Online, Dale DC; Federman DD, Eds. WebMD Inc., New York, 2000.*
Abbas et al. Cellular and Molecular Immunology 2000 Chapter 15 p. 360-362.*
Ellis, R.W. (Chapter 29 of "Vaccines" Plotkin, S.A. et al. (eds) published by W. B. Saunders company (Philadelphia) in 1988.*
(see Prasad et al 2007 Respiratory medicine vol. 101 pp. 2037-2043).*
Bowie et al (Science, 1990, 247:1306-1310).*
Parkhill, J. et al., "Complete cDNA Sequence of a Serogroup A Strain of Nesisseria Meningitidis Z2491" *Nature*, vol. 404, pp. 502-506 (2000). XP000918875.
Herve Tettelin et al., "Complete Genome Sequence of Neisseria Meningitidis Serogroup B Strain MC58", *Science*, vol. 287, pp. 1809-1815 (2000).
Database UniProt Online! Oct. 1, 2000, "Putative Periplasmic Protein". XP002331525 retrieved from EBI accession-No. UNIPROT: Q9JQZ2. Database accession No. Q9JQZ2 the whole document.

* cited by examiner

*Primary Examiner*—Robert B Mondesi
*Assistant Examiner*—Nina A Archie
(74) *Attorney, Agent, or Firm*—Hoffmann & Baron, LLP (57) ABSTRACT

Use of a novel vaccine antigen applied in a preventive or therapeutic way against diseases in general, being such disease of bacterial, viral, cancer related, or other origin.

The technical objective that this invention pursues is the development of formulations with the ability to increase the protective spectrum of existing vaccines and hence expanding it against different pathogens.

In order to achieve this goal the NMB1125 protein was isolated and identified as a component of outer membrane preparations of *Neisseria meningitidis* capable of inducing bactericidal activity.

Additionally, the gene codifying for NMB1125 protein was cloned and expressed, and the said polypeptide was purified and its immunogenicity evaluated in animal models. The sequence data from homologous genes showed, due to the high degree of conservation, its high value as a target antigen of a cross-reactive response when it is presented by different routes. Resultant formulations of this invention are of use in the pharmaceutical industry as vaccine formulations for human use.

4 Claims, 9 Drawing Sheets

Neisseria meningitides serogrupo C
>Neisseria meningitidis FAM18:orf2 718 1083 Predicted orf
          Length = 366

Score =  509 bits (257), Expect = e-145
 Identities =

Figure 8 continued

```
Neisseria meningitides serogrupo A
>Nmeningitidis Z2491:gi 7380006 1238968 1238597 putative
         periplasmic protein [Neisseria meningitidis Z2491]
         Length = 372

Score =  517 bits (261), Expect = e-148
 Identities = 261/261 (100%)
 Strand = Plus / Plus Query: 1    ctatcccgataccgtctatgaaggtttgaaaaacgacgacacttcgttgggcaagcagac 60
            ||||||||||||||||||||||||||||||||||||||||||||||||||||||||||||
Sbjct: 105  ctatcccgataccgtctatgaaggtttgaaaaacgacgacacttcgttgggcaagcagac 164

Query: 61   cgaaaagatggaaaaatactttgtggaagccggcaacaaaaaaatgaatgccgccccggg 120
            ||||||||||||||||||||||||||||||||||||||||||||||||||||||||||||
Sbjct: 165  cgaaaagatggaaaaatactttgtggaagccggcaacaaaaaaatgaatgccgccccggg 224

Query: 121  tgcgcacgcccatctgggactgctgctttcccgttcgggagacaaagagggcgcgttccg 180
            ||||||||||||||||||||||||||||||||||||||||||||||||||||||||||||
Sbjct: 225  tgcgcacgcccatctgggactgctgctttcccgttcgggagacaaagagggcgcgttccg 284

Query: 181  ccagtttgaagaagagaaaaggctgtttcccgaatcgggcgtatttatggacttcctgat 240
            ||||||||||||||||||||||||||||||||||||||||||||||||||||||||||||
Sbjct: 285  ccagtttgaagaagagaaaaggctgtttcccgaatcgggcgtatttatggacttcctgat 344

Query: 241  gaaaaccggtaaaggaggcaa 261
            |||||||||||||||||||||
Sbjct: 345  gaaaaccggtaaaggaggcaa 365

Neisseria meningitides serogrupo B
>NmeningitidisMC58:gi 7226399 1168703 1168332 hypothetical
         protein
         Length = 372

Score =  517 bits (261), Expect = e-148
 Identities = 261/261 (100%)
 Strand = Plus / Plus Query: 1    ctatcccgataccgtctatgaaggtttgaaaaacgacgacacttcgttgggcaagcagac 60
            ||||||||||||||||||||||||||||||||||||||||||||||||||||||||||||
Sbjct: 105  ctatcccgataccgtctatgaaggtttgaaaaacgacgacacttcgttgggcaagcagac 164

Query: 61   cgaaaagatggaaaaatactttgtggaagccggcaacaaaaaaatgaatgccgccccggg 120
            ||||||||||||||||||||||||||||||||||||||||||||||||||||||||||||
Sbjct: 165  cgaaaagatggaaaaatactttgtggaagccggcaacaaaaaaatgaatgccgccccggg 224

Query: 121  tgcgcacgcccatctgggactgctgctttcccgttcgggagacaaagagggcgcgttccg 180
            ||||||||||||||||||||||||||||||||||||||||||||||||||||||||||||
Sbjct: 225  tgcgcacgcccatctgggactgctgctttcccgttcgggagacaaagagggcgcgttccg 284
```

Figure 8 continued

```
Query: 181
       ccagtttgaagaagagaaaaggctgtttcccgaatcgggcgtatttatggacttcctgat 240
           ||||||||||||||||||||||||||||||||||||||||||||||||||||||||||||
Sbjct: 285 ccagtttgaagaagagaaaaggctgtttcccgaatcgggcgtatttatggacttcctgat 344

Query: 241 gaaaaccggtaaaggaggcaa 261
           |||||||||||||||||||||
Sbjct: 345 gaaaaccggtaaaggaggcaa 365

Neisseria meningitides serogrupo B (NMB1163)
>NmeningitidisMC58:gi_7226361 1136667 1136296 hypothetical
           protein
           Length = 372

Score =  517 bits (261), Expect = e-148
 Identities = 261/261 (100%)
 Strand = Plus / Plus Query: 1   ctatcccgataccgtctatgaaggtttgaaaaacgacgacacttcgttgggcaagcagac 60
           ||||||||||||||||||||||||||||||||||||||||||||||||||||||||||||
Sbjct: 105 ctatcccgataccgtctatgaaggtttgaaaaacgacgacacttcgttgggcaagcagac 164

Query: 61  cgaaaagatggaaaaatactttgtggaagccggcaacaaaaaaatgaatgccgccccggg 120
           ||||||||||||||||||||||||||||||||||||||||||||||||||||||||||||
Sbjct: 165 cgaaaagatggaaaaatactttgtggaagccggcaacaaaaaaatgaatgccgccccggg 224

Query: 121 tgcgcacgcccatctgggactgctgctttcccgttcgggagacaaagagggcgcgttccg 180
           ||||||||||||||||||||||||||||||||||||||||||||||||||||||||||||
Sbjct: 225 tgcgcacgcccatctgggactgctgctttcccgttcgggagacaaagagggcgcgttccg 284

Query: 181 ccagtttgaagaagagaaaaggctgtttcccgaatcgggcgtatttatggacttcctgat 240
           ||||||||||||||||||||||||||||||||||||||||||||||||||||||||||||
Sbjct: 285 ccagtttgaagaagagaaaaggctgtttcccgaatcgggcgtatttatggacttcctgat 344

Query: 241 gaaaaccggtaaaggaggcaa 261
           |||||||||||||||||||||
Sbjct: 345 gaaaaccggtaaaggaggcaa 365
```

PROTEIN NMB1125 AND USE THEREOF IN PHARMACEUTICAL FORMULATIONS

This application is a U.S. National Phase Application of International Application No. PCT/CU04/000015 filed on Dec. 2, 2004. The specification of International Application No. PCT/CU04/000015 is hereby incorporated by reference.

This application asserts priority to Cuban Application No. CU 2003/0285 filed on Dec. 3, 2003. The specification of Cuban application No. CU 2003/0285 is hereby incorporated by reference.

BACKGROUND OF THE INVENTION

The present invention is related to field of medicine, particularly to the development of new vaccine formulations of preventive or therapeutic application, which allows an increase in the quality of the immune response against vaccine antigens of diseases from different sources.

*Neisseria meningitidis*, a Gram-negative diplococcus which only known host is man, is the causal agent of meningococcal meningitis. Usually this bacterium is found in asymptomatic carriers among the normal population, being this niche the most common source for its microbiological isolation.

On world basis, small children less than two years of age are the more susceptible population for contracting meningococcal meningitis, however, young adults and normal adult population may also be affected.

Untreated meningococcal disease has a fatal course for most affected individuals, and vaccination could prevent this situation, by halting the events as early as at the bacterial colonization phase.

Several strategies have been developed with the aim of obtaining a vaccine able to fulfill the needed requirements in order to induce protection against this disease in general population. For this purpose, capsular antigens have been taken into account, since their immunological specificities have allowed the classification into serogroups of this microorganism. Five of these serogroups have been defined as responsible of most of the clinical cases of meningococcal disease all around the world. Serogroup A is the principal cause of epidemics in sub-Saharan Africa. Serogroups B and C are associated, in most cases, to the occurrences in developed nations. Serogroups Y and W135 are common in most of the recurrent cases of the disease, and they are prevalent in some areas of USA, with a marked increase in the last few years. From this data, it is obvious the reason of the use, study, and evaluation of capsular polysaccharides as vaccine candidates. A tetravalent vaccine, based on capsular polysaccharides, conferring protection against serogroups A, C, Y, and W-135 has been licensed in United States. Antibodies elicited after vaccination are serogroup-specific (Rosenstein N. et al. 2001. *Meningococcal disease*. N. Engl. J. Med, 344, 1378-1388).

Serogroup B, which is different from the rest, continues to be a significant cause of endemic and epidemic meningococcal disease, and this is mainly due to the complete lack of efficient vaccines against it. It has been noted that capsular polysaccharide B is poorly immunogenic, plus the existence of the theoretical risk for a vaccine based on this compound to induce immuno-tolerance and autoimmunity because of its structural similarity to oligosaccharide chains that are present in human neural fetal structures. (Finne J. et al. 1987. *An IgG monoclonal antibody to group B meningococci cross-reacts with developmentally regulated polysialic acid units of glycoproteins in neural and extraneural tissues*. J. Immunol, 138: 4402-4407). Therefore, the development of vaccines against serogroups B is concentrated in the use of sub-capsular antigens.

Outer Membrane Proteins and Vesicle Vaccines

Initial attempts, in the 70s, to produce vaccines based on outer membrane proteins were based on the LPS depletion of outer membrane protein preparations by detergent (Frasch C E and Robbins J D. 1978. *Protection against group B meningococcal disease. III. Immunogenicity of serotype 2 vaccines and specificity of protection in a guinea pig model*. J Exp Med 147(3):629-44). The outer membrane proteins, OMPs, were then precipitated to produce aggregates suspended in sodium chloride. Despite promising results in animal studies, these vaccines failed to induce bactericidal antibody in either adults or children (Zollinger W D, et al. 1978. *Safety and immunogenicity of a Neisseria meningitidis type 2 protein vaccine in animals and humans*. J. Infect. Dis. 137(6):728-39), the poor performance of these vaccines was largely attributed to the loss of tertiary structure that accompanied precipitation. The next logical step was, therefore, to produce a vaccine with proteins displayed in their native conformation in the form of vesicles of outer membrane (Zollinger W D, et al. 1979. *complex of meningococcal group B polysaccharide and type 2 outer membrane protein immunogenic in man*. J. Clin. Invest. 63(5):836-48, Wang L Y and Frasch C E. 1984. *Development of a Neisseria meningitidis group B serotype 2b protein vaccine and evaluation in a mouse model*. Infect Immun. 46(2):408-14136).

These outer membrane vesicle vaccines were significantly more immunogenic than the OMP aggregates and immunogenicity was shown to be further enhanced by adsorption to the adjuvant aluminium hydroxide (Wang L Y and Frasch C E. 1984. *Neisseria meningitidis group B serotype 2b protein vaccine and evaluation in a mouse model*. Infect Immun. 46(2):408-14136).

A number of efficacy trials have been carried out using soluble outer membrane vesicle vaccines of different formulations. The two vaccines most extensively studied were developed in the 1980s in response to outbreaks of disease in Cuba (Sierra G V et al. 1991. *Vaccine against group B Neisseria meningitidis: protection trial and mass vaccination results in Cuba*. NIPH Ann Dis. 14(2):195-210) and Norway (Bjune G, et al. 1991. *Effect of outer membrane vesicle vaccine against group B meningococcal disease in Norway*. Lancet. 338(8775):1093-6), respectively. The OMV vaccine produced by the Finlay Institute in Cuba (commercially marketed as VA-MENGOC-BC) is produced from strain B:4: P1.19,15 with serogroup C polysaccharide and a preparation of high molecular weight OMPs and is adsorbed to aluminium hydroxide (Sierra G V et al. 1991. *Vaccine against group B Neisseria meningitidis: protection trial and mass vaccination results in Cuba*. NIPH Ann Dis. 14(2):195-210). This vaccine contributed to the rapid decline of the epidemic in Cuba (Rodriguez A P, et al. *The epidemiological impact of antimeningococcal B vaccination in Cuba*. 1999. Mem Inst Oswaldo Cruz. 94(4):433-40).

The vaccine produced by the Norwegian National Institute for Public Health (NIPH) was similarly intended initially for use during a period of hyperendemic disease caused by another organism from the ET-5 clone (B:15:P1.7,16). It was also a monovalent vaccine produced from purified outer membrane vesicles adsorbed onto aluminium hydroxide (Bjune G, et al. 1991. *Effect of outer membrane vesicle vaccine against group B meningococcal disease in Norway*. Lancet. 338(8775):1093-6).

Outer membrane vesicle vaccines appear to effectively present outer membrane proteins in a sufficiently natural conformation to allow the generation of functional bactericidal antibodies, at least in teenagers and adults. The antibody responses generated have also been shown to increase opsonophagocytosis of meningococci. The precise formulation of the vaccines (i.e. OMP content, LPS content and the presence or absence of adjuvant) has a significant impact on immunogenicity (Lehmann A K, et al. 1991. *Immunization against serogroup B meningococci. Opsonin response in vaccinees as measured by chemiluminescence*. APMIS. 99(8): 769-72, Gomez J A, et al. 1998. *Effect of adjuvants in the isotypes and bactericidal activity of antibodies against the transferrin-binding proteins of Neisseria meningitidis*. Vaccine. 16(17):1633-9, Steeghs L, et al. 1999. *Immunogenicity of Outer Membrane Proteins in a Lipopolysaccharide-Deficient Mutant of Neisseria meningitidis: Influence of Adjuvants on the Immune Response*. Infect Immun. 67(10):4988-93).

The antigenic profile of disease isolates also changes rapidly and a vaccine with coverage of only a limited number of selected strains is likely to become ineffective within a few years unless the vaccine composition is changed to mirror local epidemiology.

At present OMV vaccines have been used more widely than any other serogroup B vaccine and are potentially useful in the context of outbreaks of disease caused by a single PorA type.

The immunogens that generate cross-reactivity between strains have yet to be fully defined. Studies of post-vaccination sera from both Finlay Institute and NIPH vaccine trials suggested that antibodies against both PorA (P1, the class 1 serosubtype protein) and OpcA (another major OMP, formerly known as Opc) (Wedege E, et al. 1998. *Immune Responses against Major Outer Membrane Antigens of Neisseria meningitidis in Vaccinees and Controls Who Contracted Meningococcal Disease during the Norwegian Serogroup B Protection Trial*. Infect Immun. 66(7): 3223-31), were both important in the mediation of serum bactericidal activity (wilh PorA mosl immunogenic) both these antigens show marked strain to strain variability.

The prominence of PorA protein and the significant level of variability in this protein, which appears to undergo continuous variation both between and during outbreaks (Jelfs J, et al. 2000. *Sequence Variation in the porA Gene of a Clone of Neisseria meningitidis during Epidemic Spread*. Clin Diagn Lab Immunol. 7(3):390-5) in epitopes to which most of the bactericidal activity in post-vaccination (and post-disease) is directed enhanced concerns that protection offered by single strain (monovalent) OMV-based vaccines might be serosubtype restricted (i.e. dependent on The PorA type).

In an attempt to overcome this potential problem, an OMV vaccine was developed in The Netherlands at RIVM that contained PorA proteins from six different prevalent pathogenic isolates (Van Der Ley P and Poolman J T. 1992. *Construction of a multivalent meningococcal vaccine strain based on the class 1 outer membrane protein*. Infect Immun. 60(8):3156-61, Claassen I, et al. 1996. *Production, characterization and control of a Neisseria meningitidis hexavalent class 1 outer membrane protein containing vesicle vaccine*. Vaccine. 14(10):1001-8). In this case the vaccine vesicles were extracted from two variants of the well-characterized H44/76 strain which had been genetically engineered lo express three separate PorA proteins.

The Search for a Universal Antigen

It is clear that outer membrane proteins (OMP) can induce a functional immune response against serogroup B disease but that none of the vaccines so far developed are universally protective due to the great heterogeneity of the surface exposed regions of the outer membrane proteins. The modest cross-reactive immunity induced by the outer membrane vesicles (OMV) vaccines has fuelled the search for an outer membrane antigen (or group of antigens), which induces functional antibodies and which is present on all meningococcal strains. Such antigens, if they were present on all strains irrespective of serogroup, might form the basis of a truly universal meningococcal vaccine, which would eliminate the potential problem of capsular switching on pathogenic strains following polysaccharide vaccination.

Once it became apparent that the variability of the immunodominant PorA protein would limit its use as a universal vaccine, a number of the other major outer membrane proteins were considered for their vaccine potential and several of these are under further development. Those which have been considered include class 5 proteins (OpcA), NspA and iron regulated proteins (TbpA and B, FbpA, FetA). TbpB forms part of the transferrin binding complex with TbpA. Recent work suggests that TbpA has both a greater functional role in iron binding (Pintor M, et al. 1998. *Analysis of TbpA and TbpB functionality in defective mutants of Neisseria meningitidis*. J Med Microbiol 47(9): 757-60) and is a more effective immunogen than TbpB.

A highly conserved minor outer membrane protein has been discovered via a novel technique using combinations of outer membrane protein preparations from different meningococcal strains to immunize mice (Martin D, et al. 1997. *Highly Conserved Neisseria meningitidis Surface Protein Confers Protection against Experimental Infection*. J Exp Med 185 (7): 1173-83). The B cells from the mice were used to produce hybridomas which were then screened for cross-reactivity against multiple strains of meningococci. One highly cross-reactive monoclonal antibody was found to bind to a 22 kDa outer membrane protein that was designated NspA. Immunization with recombinant NspA protein was shown to induce a cross-reactive bactericidal response in mice against strains from serogroups A-C. Vaccination also protects mice against lethal meningococcal infection (Martin D, et al. 1997. *Highly Conserved Neisseria meningitidis Surface Protein Confers Protection against Experimental Infection*. J Exp Med 185 (7): 1173-83). Comparison of NspA sequences among genetically divergent meningococcal strains demonstrates that the protein is highly conserved (97% homology) (Cadieux N, et al. 1999. *Bactericidal and Cross-Protective Activities of a Monoclonal Antibody Directed against Neisseria meningitidis NspA Outer Membrane Protein*. Infect Immun 67 (9): 4955-9).

The presence of NspA was detected by ELISA on 99.2% of tested strains from serogroups A-C using anti-NspA monoclonal antibodies (Martin D, et al. 1997. *Highly Conserved Neisseria meningitidis Surface Protein Confers Protection against Experimental Infection*. J Exp Med 185 (7): 1173-83). These monoclonal antibodies have been shown to be bactericidal against numerous strains of meningococci and are able to reduce meningococcal bacteraemia in a mouse model (Cadieux N, et al. 1999. *Bactericidal and Cross-Protective Activities of a Monoclonal Antibody Directed against Neisseria meningitidis NspA Outer Membrane Protein*. Infect Immun 67 (9): 4955-9). Although this data appears to suggest that NspA is a promising vaccine candidate that is able to protect across serogroup boundaries, polyclonal anti-recombinant NspA serum from mice does not bind to the surface of around 35% of pathogenic serogroup B meningococcal strains despite the presence of the nspA gene in these organisms (Moe G R et al. 1999. *Differences in Surface Expression of NspA among Neisseria meningitidis Group B Strains.* Infect Immun 67 (11): 5664-75).

Antigen Presentation and Vaccine Formulation.

Earlier work has suggested that the form in which the antigens are presented is likely to be critical. The epitopes on membrane bound proteins are often dependent on maintenance of the correct tertiary structure and this in turn is frequently dependent on the hydrophobic membrane bound domains. It has been shown that the preparations of outer membrane proteins elicit immunity in humans only when presented in vesicle form (Zollinger W D, et al. 1979. *complex of meningococcal group B polysaccharide and type 2 outer membrane protein immunogenic in man.* J Clin Invest 63 (5): 836-48, Zollinger W D, et al. 1978. *Safety and immunogenicity of a Neisseria meningitidis type 2 protein vaccine in animals and humans.* J Infect Dis 137 (6): 728-39).

Single protein vaccines have been used in the field for decades and generally exhibit good stability. If presentation in the form of vesicles is required, to allow the antigens to remain membrane bound, stability and reproducibility may be difficult to guarantee. The immunogenicity and reactogenicity of outer membrane vesicles may vary with alterations in the amount of protein and LPS removed in the purification processes. A substantial body of experience in vesicle production has accrued in OMV vaccine manufacture, however, and the currently produced vaccines are subject to thorough quality control. Construction of entirely synthetic liposome vesicles may allow further optimization and standardization of such vaccines (Christodoulides M, et al. 1998. *Immunization with recombinant class 1 outer-membrane protein from Neisseria meningitidis: influence of liposomes and adjuvants on antibody avidity, recognition of native protein and the induction of a bactericidal immune response against meningococci.* Microbiology 144(Pt 11):3027-37). In other words, outer membrane proteins have been presented both, in vesicles and as pure expressed proteins, and the development of antibody responses has been modest. Main efforts so far have concentrated on intramuscular injection of meningococcal vaccine, leading to the production of systemic IgG. However, in meningococcal disease where invasion of the host is via the nasal epithelium, the production of secretory IgA may also be important.

The *N. meningitidis* Genome Sequence

The genome sequences of MC58 (a serogroup B meningococcus) (Tettelin H, et al. 2000. *complete Genome Sequence of Neisseria meningitidis Serogroup B Strain MC58.* Science 287 (5459): 1809-15172) y and of Z2491 (a serogroup A strain) (Parkhill J, et al. 2000. *complete DNA sequence of a serogroup A strain of Neisseria meningitidis Z2491.* Nature 404 (6777):502-6173) were elucidated and published during 2000. The availability of the annotated gene sequences should have a dramatic influence on meningococcal vaccine research. While the MC58 genome sequencing was in progress, Pizza et al. began identifying the open reading frames that were predicted to encode either membrane bound, surface exposed or exported proteins. They identified 570 such ORFs, amplified them via the polymerase chain reaction and cloned them into *Escherichia coli* to allow expression of the encoded proteins as either His-tagged or glutathione S-transferase fusion proteins (Pizza M, et al. 2000. *Identification of Vaccine Candidates Against Serogroup B Meningococcus by Whole-Genome Sequencing.* Science 287 (5459): 1816-20). The 61% (350) of the selected ORFs were successfully expressed, those which failed to express were often those containing more than one hydrophobic trans-membrane domain (possibly excluding a number of outer membrane bound proteins). The recombinant proteins were purified and used to vaccinate mice. The immune sera were then assessed for surface binding to multiple meningococcal strains by enzyme linked immunosorbent (ELISA) assay and flow cytometry and for bactericidal activity against two strains using the serum bactericidal assay. Finally seven proteins were selected for further study on the basis of a positive response in all three assays. Trial vaccine formulations using a number of these proteins in combination with adjuvants have been shown to induce significant bactericidal tires against the homologous meningococcal strain (MC58) in mice, but none of the proteins induced SBA litres as high as an MC58 outer membrane vesicle vaccine (Giuliani M M, et al. 2000. Proceedings 12th IPNC. p. 22). On the other hand, there is some evidence that combinations of these proteins may exhibit higher immunogenicity in mice than single proteins (Santini L. et al. 2000. Proceedings 12th IPNC. p. 25). The numerous open reading frames which were excluded during this work, perhaps through failure of protein expression or modification of their immunological properties, may also have vaccine potential and require further investigation.

Vaccine components may be selected more effectively once an understanding of the contribution of individual antigens to the pathogenesis of *N. meningitidis* has been gained. The antigens themselves may make effective vaccine candidates or, alternatively, the attenuated mutants could be considered as vaccine constituents. In this direction, the use of vaccine candidates with a high degree of sequence conservation among several species of pathogenic microorganisms, could provide a solution to the multiple diseases they might cause in the case that these candidates induce a convenient response through the action of the immune system.

The technical aim that this invention pursues is the development of vaccine formulations capable of increasing and/or broadening the induced immune response against different pathogens or against a wide range of individual pathogen variants being these pathogens of cancer, bacteria, viral or any other origin.

DESCRIPTION OF THE INVENTION

In the work object of the present invention it is reported, for the first time, the use of the NMB1125 protein as a component of a vaccine formulation with therapeutic or preventive character against the meningococcal disease or any infection caused by a member of the *Neisseria* genus.

The novel character of this invention consists in the use, previously unreported, of the NMB1125 protein in formulations with new properties, able to induce a systemic and mucosal immune response of broad-spectrum protection, due to the conserved character of this protein in different isolates of *Neisseria meningitidis* and *Neisseria gonorrhoeae*.

EXAMPLES

The present invention is described herein through the examples which despite of being informative about the invention itself they do not represent, by any mean, a limit to the scope of the said invention.

Example 1

Detection of NMB1125 Protein in Serogroup B
*Neisseria meningitidis* Outer Membrane Vesicles
Preparations With the aim of studying proteins that are present in serogroup B *Neisseria meningitidis* (strain B:4:P1.19,15) outer membrane vesicles, a bi-dimensional electrophoresis was carried out according to a method described elsewhere (Görg A, et al. 1985. Electrophoresis 6:599-604). Subsequently an enzymatic digestion was made upon the gel extracted proteins using trypsin (Promega, Madison, Wis., U.S.). Peptides generated after digestion were extracted into solution by using microcolumns (ZipTips, Millipore, Mass., U.S.). For mass spectometry analysis peptides were eluted from microcolumns with acetonitrile 60%, formic acid 1% followed by an immediate application into nanotips (Protana, Denmark).

Measurements were carried out in a hybrid mass spectrometer with cuadrupole and time of flight (QTof-2™, Manchester, United Kingdom), fitted with an ionization source (nanoESI). Mass spectrometry data were acquired in a w/z range of 400-2000 in 0.98 seconds and using 0.02 seconds between scannings. Data acquisition and data processing were carried out using the MassLynx program (version 3.5, Micromass). Protein identification based on mass spectrum data was carried out using the ProFound program (Zhang W and Chait B T. 2000. *ProFound: an expert system for protein identification using mass spectrometric peptide mapping information*. Anal Chem 72:2482-2489. prowl.rockefeller.edu/cgi-bin/ProFound). The search was subscribed to the genes and derived protein sequences contained in the SwissProt database (ebi-.ac.uk/swissprot/) and NCBI (http://www.ncbi.nlm.nih-.gov/), considering the oxidation of methionines, deamidation and carboxyamidomethylation of cysteines as possible modifications to be encountered.

Identification of proteins based on the mass spectra was carried out with the MASCOT program (Perkins D N, et al. 1999. *Probability-based protein identification by searching sequence databases using mass spectrometry data*. Electrophoresis 20:3551-3567. matrixscience.com/). Search parameters included cysteine modifications as well as oxidations and deamidations.

Starting from the analysis of results obtained from the identification of proteins present in preparations of outer membrane vesicles, the NM1125 protein was selected to be evaluated as possible vaccine candidate, from which one peptide was identified by mass spectrometry.

Example 2

Homology Analysis of NMB1125 Protein with
Reported Gene Products in Available Databases For the analysis of the homology of NM1125 protein with other gene products, a homology based search was carried out in the NCBI sequence data base using the BLAST program (Altschul S F, et al. 1990. *Basic local alignment search tool*. J Mol Biol 215:403-410, ncbi.nlm.nih.gov/BLAST/). The results obtained after this procedure were marked as homologous, and beside the proteins reported in the published Neisserial genomes, several gene products marked as hypothetical proteins from different organisms, like *Ralstonia, Yersinia* and *Pseudomonas* species, were recognized.

The high degree of conservation of these proteins in these genomes has lead to the generation of an orthologous group with a conserved domain reported at NCBI database [(gnl|CDD|13507, COG4259, Uncharacterized protein conserved in bacteria [Function unknown)], indicating the existence of a possible phylogenetic link and common ancestry among them.

The analysis of the genomic environment of the gene that codifies for NM1125 was carried out using the MBGD database (Uchiyama, I. 2003. *MBGD: microbial genome database for comparative analysis*. Nucleic Acids Res. 31, 58-62.), and revealed a conserved genetic organization with these genes in the previously mentioned microorganisms which, in conjunction with the previous data, prompted us to conclude that they are effectively homologous in their respective genomes.

Example 3

Cloning and Expression of the NMB1125 Gene, Codifying for NMB1125 Protein from *N. meningitidis* in *Escherichia coli*

In order to clone and express the NM1125 gene, the pM-100 cloning vector was employed. This vector allows the cloning to be carried out using different restriction enzymes and the generation of high expression levels of heterologous proteins in the form of inclusion bodies in *E. coli*.

Figure 1:
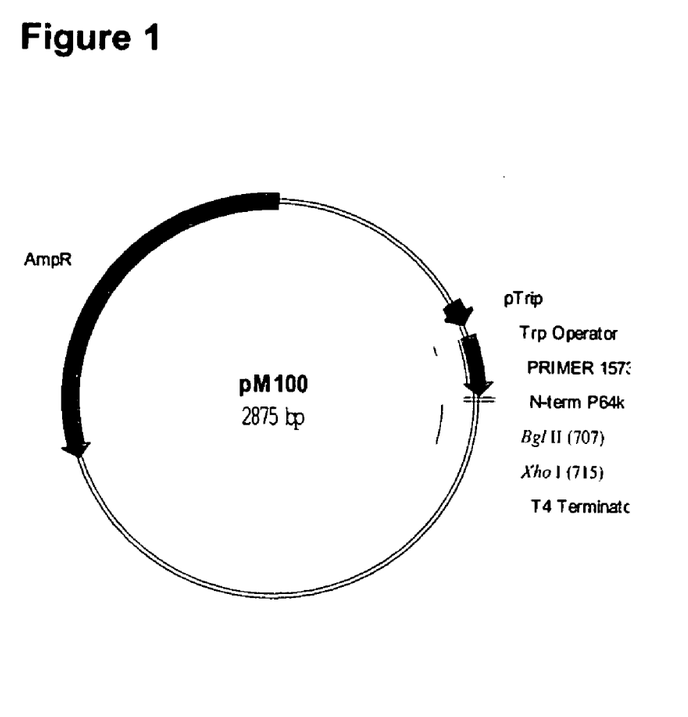
FIG. 1. Cloning vector pM100 employed in the cloning and expression of protein NMB1125. pTrip, tryptophan promoter; N-term P64k, P-64k N-terminal fragment; T4 Terminator, Transcriptional terminator T4 phage.

The pM-100 vector (FIG. 1) have the following elements: tryptophan promoter, gene segment codifying for the 47 amino acid stabilizing sequence from Nt-fragment of P64 kDa from *N. meningitidis* strain B:4:P1.19,15, sequence of bacteriophage T4 transcriptional terminator, and the sequence of the gene that confers resistance to ampicillin as selection marker.

From the nucleotide sequence codifying for NMB1125 protein (Example 1) two primers were designed (7738 y 7739) in order to amplify the segment of this gene, without the sequence that codifies for the predicted signal peptide, from the strain B:4:P1.19,15 genomic DNA

```
                                              (Seq. ID. No. 1)
              BglII
 7738: 5'TTAGATCTCTATCCCGATACCGTCTATGAAGG '3

(Seq. ID. No. 2)
 7739: 5'AAGCTCGAGTCGTTTGCCTCCTTTACC 3'
              XhoI
```

For the prediction of signal peptide the SignalP World Wide Web server (cbs.dtu.dk/services/SignalP-2.0) was employed. After PCR amplification of the NMB1125 gene (Randall K, et al. 1988. Science 42394:487-491) employing primers 7738 and 7739, the PCR product was digested using BglII and XhoI restriction enzymes, and cloned into vector previously digested pM-100 cloning vector. The final construction is showed in FIG. 2, and the NMB1125 protein is expressed as a fusion protein to the Nt-segment of P64 kDa protein. Sequencing of the cloned gene NMB1125 was carried out using ALFexpress II automatic sequencer (Thermo Sequenase™ Cy™ 5 Dye Terminador Kit, Amersham Biosciences) and oligonucleotides 1573 (Seq. ID. No. 8) and 6795 (Seq. ID. No. 9), that bind the sequence of the P64 stabilizer and T4 transcriptional terminator, respectively. The plasmid generated herein was designated pM-238 for its posterior use.

Figure 2:
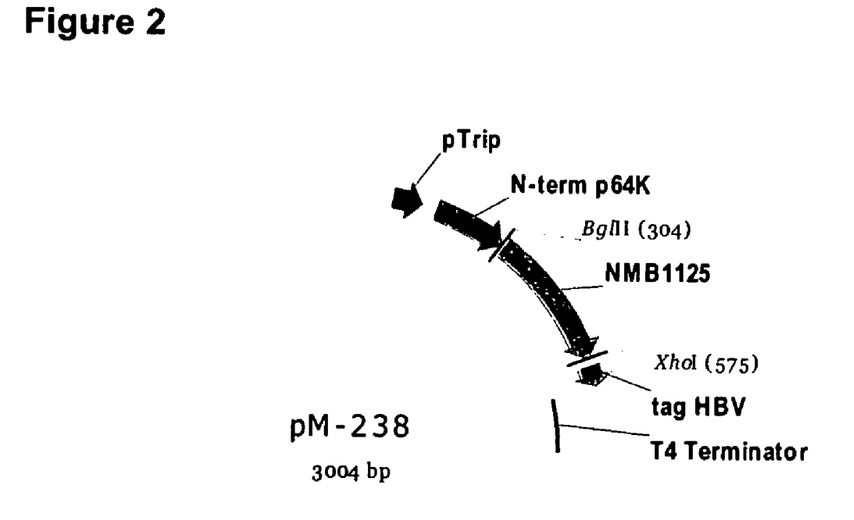
FIG. 2. Final construction of nucleotide sequence of the gene NMB1125 in pM100 vector.
Figure 3:
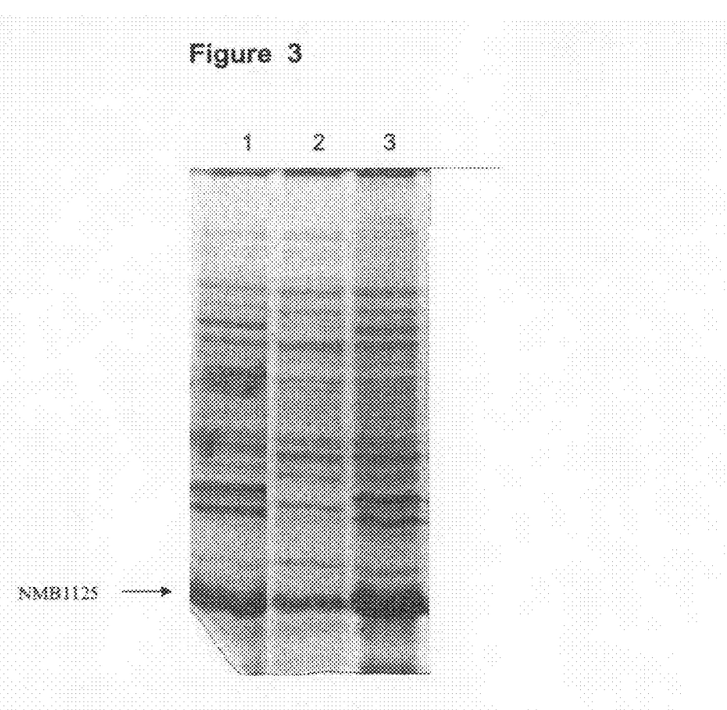
FIG. 3. SDS-PAGE analysis of fractions obtained from cellular disruption. Lane 1, total cells; Lane 2, cellular pellet; Lane 3, supernatant.
Figure 4:
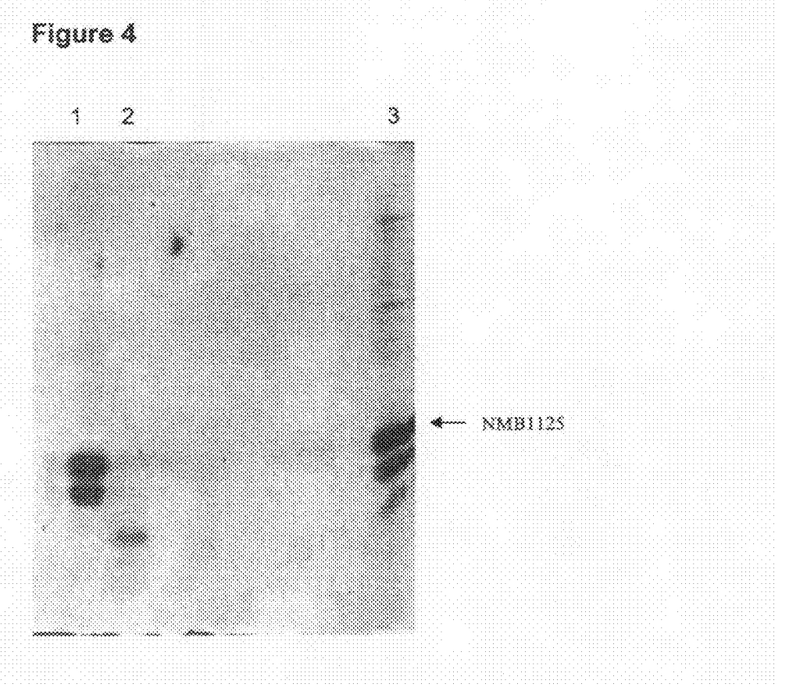
FIG. 4. SDS-PAGE analysis of purification process of NMB1125 from the disruption supernatant. Lane 1, resultant protein; Lane 2, contaminant protein of lower molecular weight found in a different chromatography fraction. Lane 3, sample before application.

For the expression of the NMB1125 gene the GC366 *E. coli* strain was transformed by the chemical method with the pM-238 plasmid (FIG. 2). The expression experiment was carried out in minimal media (M9) (Miller J H. 1972. Experiments in Molecular Genetics, Cold Spring Harbor Laboratory Press, NEW York, USA) supplemented with 1% glycerol, 1% casein hydrolisate, 0.1 mM $CaCl_2$, 1mM $MgSO_4$ and 50 ug/mL ampicillin. Bacterial cultures were incubated 12 hours at 37° C. and 250 rpm. Grown cultures were centrifugated and ultrasonic disruption of the cellular pellet was performed (IKA LABORTECHNIK). Fractions from pellet and supernatant were analyzed by SDS-PAGE (Laemmli U K. 1970. *Cleavage of structural proteins during the assembly of the head of bacteriophage T*4. Nature 277:680) plus stain with Coomassie Brilliant Blue R-250. The percent of expression was carried out by gel densitometry (LKB Bromma 2202 Ultrascan laser densitometer; Amersham Pharmacia Biotech, United Kingdom). The NMB1125 protein was obtained from the supernatant fraction, being about the 60% of total protein content of this fraction (FIG. 3). The protein containing fraction was dialyzed against Buffer A (25 mM Tris-hydroxymethyl aminomethane) from which the NMB1125 protein was purified by ionic exchange chromatography using a monoQ 5/5 column (Amersham Biosciences) with a gradient from 0 to 100% of NaCl in 1 h [Buffer A as equilibrium buffer and Buffer B (Buffer A+1M NaCl) as gradient buffer] after which an 80% pure protein was obtained as it is shown in FIG. 4.

Example 4

Evaluation of the Immune Response Induced after Immunization with NMB1125 Protein by Intra-peritoneal and Intra-nasal Routes To evaluate the immunogenicity of the protein NMB1125, an immunization experiment was designed and conducted in mice, where the same protein was administered by two different methods. The first consisted in to extract the band from a polyacrylamide gel (Castellanos L, et al. 1996. *A procedure for protein elution from reverse-stained polyacrylamide gels applicable at the low picomole level: An alternative route to the preparation of low abundance proteins for microanalysis*. Electroforesis 17: 1564-1572) and the second one was referred in Example 3, and the product was denoted as semi-purified protein.

With these preparations, female Balb/C mice (8-10 weeks-old) were immunized, once divided in 4 groups of 8 mice, each. Three immunizations were applied by intra-nasal or intra-peritoneal route, with 15 days-interval in between. The protein administered by intra-peritoneal route was emulsified with Freund's adjuvant. In Table 1 is described the composition of the immunogens:

TABLE 1

| Groups of Balb/C mice employed for immunization | | | |
|---|---|---|---|
| Groups | Prot. extracted from gel | Semi-purified protein | Route |
| 1 | 50 µg | — | i.n |
| 2 | — | 50 µg | i.n |
| 3 | 10 µg | — | i.p |
| 4 | — | 10 µg | i.p |

Figure 5:
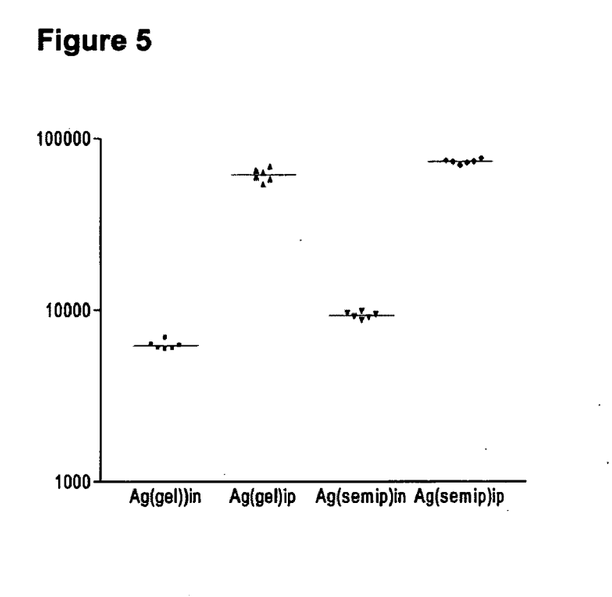
FIG. 5. Antibody levels (IgG) against recombinant protein NMB1125, obtained after mice immunization by intra-nasal or intra-peritoneal route. ELISA results are represented, and expressed, as the inverse of the highest dilution that duplicates the value of pre-immune sera.

The antibody titers (IgG) against the recombinant protein and the homologous protein present in the bacterium were determined by an ELISA, in serum samples taken after the third inoculation. In FIG. 5, the antibody titers against the recombinant protein of individual animals are shown. Antibody levels were determined after the second inoculation, although they were higher after the third inoculation. Moreover, the immunoidentification by Western blotting was done, where the respective protein band was recognized. The groups immunized by intra-peritoneal route had titers significantly higher than those elicited by intra-nasal route. For the statistical analysis of the results, the non-parametric analysis of variance of Kruskal-Wallis was used, due to the non homogeneity of the variance in the groups, according to the Bartlett's test. The Multiple comparison test of Dunn was employed to compare the means of each treatment.

Figure 6:
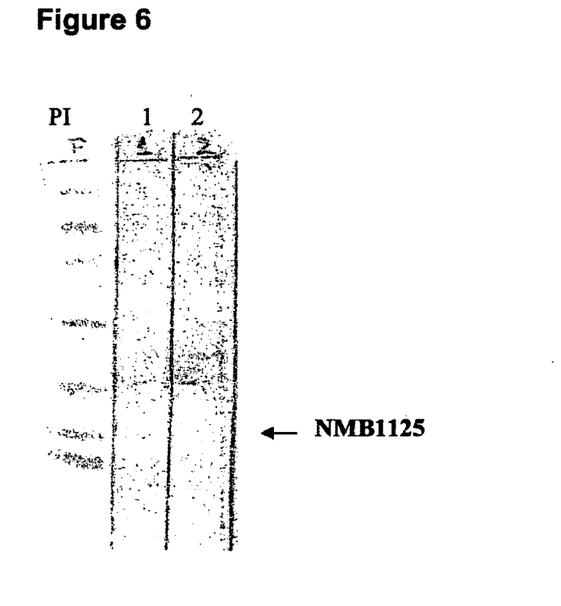
FIG. 6. Western blotting of NMB1125 protein present in *N. meningitidis* OMVs using sera from immunized mice with the recombinant protein. The immuno-identified NMB1125 is highlighted.
Figure 7:
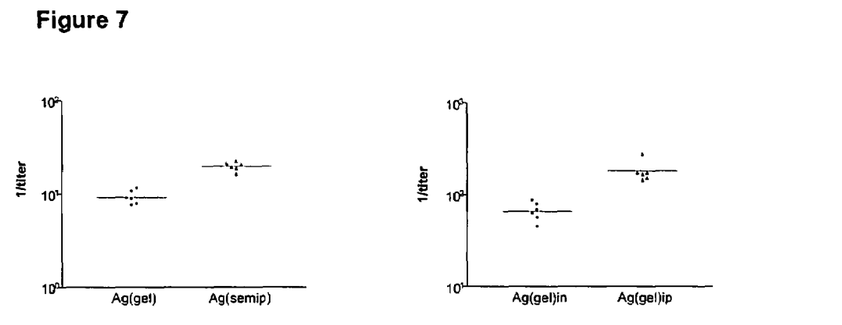
FIG. 7. IgA antibody response against recombinant protein NMB1125, at mucosal level, in mice immunized by intra-nasal route. Results are presented as the inverse of the highest dilution that duplicates the value of pre-immune sera. (A) IgA antibody response in saliva. (B) IgA antibody response in lung washes.

The sera obtained after the immunization with the recombinant protein recognized the natural protein present in a preparation of outer membrane protein (OMP) of strain CU385. These results are represented in FIG. 6. To analyze the mucosal response saliva samples and lung washes were evaluated. FIG. 7 show only the groups immunized by intra-nasal route. An increase in the IgA titer was observed in the group that received the semi-purified protein.

Example 5

Characterization of the Sequence of the Gene Codifying for Protein NMB1125 in Different Strains of *N. meningitidis*

Figure 8:
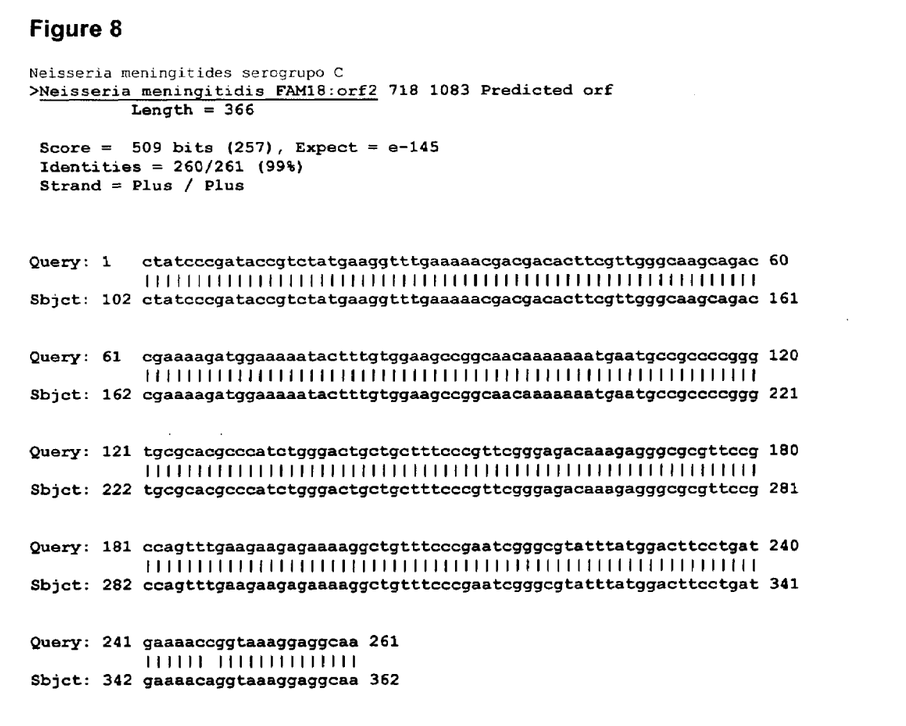
FIG. 8. Results of homology searches between NMB1125 protein (query) and annotated sequences in genomes from different serogroups of *Neisseria meningitidis* ("Sbjct") using BLAST.

To analyze the conservation of the sequence of the gene which codifies for protein NMB1125 among different strains of *Neisseria meningitidis* a similarity search was conducted with the genomes of *Neisseria meningitidis* (serogroups A, B and C) annotated in the data base of NCBI (NC 003116.1, NC 003112.1, NC 003221, SANGER 135720|Contig1) employing the program BLAST (Altschul S F, et al. 1990. *Basic local alignment search tool*. J Mol Biol 215:403-410. ncbi.nlm.nih.gov/BLAST/). FIG. 8 shows the results of the sequence comparison for those sequences that produced a significant alignment in each of the analyzed genomes. Sequences in groups A and B have 100% identity with the sequence obtained for the gene codifying for protein NMB1125 (Seq. ID. No. 3), and 99% identity in serogroup C. In addition, the sequence of the referred gene was determined for 3 Cuban isolates (Seq. ID. No. 5-7), which belong to serogroup B (B:4:P1.19,15) and a sequence alignment was done by using the ClustalX program (http://www.ebi.ac.uk/clustalw/). The results of the alignment show that there is a great conservation in the nucleotide sequence of the gene NMB1125 among the analyzed strains.

The use of the protein NMB1125 as a vaccine candidate, taking into account the high degree of similarity existing among the sequences previously mentioned, would allow the generation of an effective immune response, with a broad-spectrum protection (due to the cross reactivity) against the meningococcal disease.

Example 6

Characterization of the Immune Response with Broad-Spectrum Action Induced by the Immunization of Balb/C Mice with the Protein NMB1125

To evaluate if the immunization with protein NMB1125 induced a response broadly cross-reactive with other strains of *Neisseria*, an ELISA was done. The polystyrene plates were coated with whole cells of 7 strains of *Neisseria*, which belong to different serotypes and serosubtypes. The plates were incubated with pooled sera obtained against the protein NMB1125, by two routes of immunization, as described in Example 4.

Figure 9:
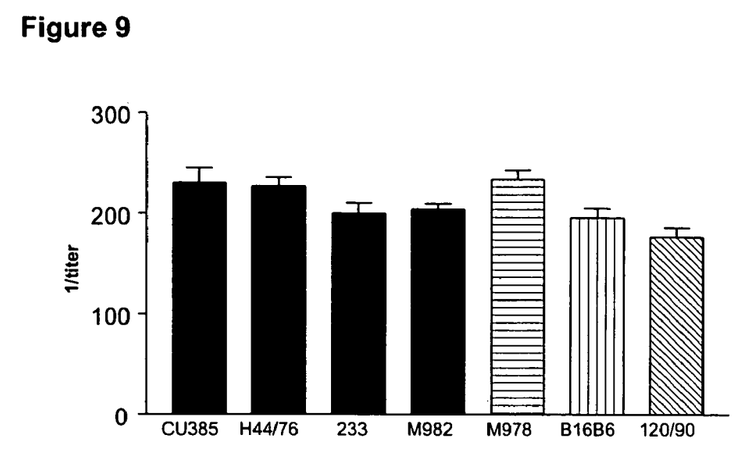
FIG. 9. Recognition of NMB1125 protein in different strains of *N. meningitidis*, by sera elicited against the recombinant antigen. In the graphic only are shown the results obtained when using semi-purified protein by intra-peritoneal route, however a similar behavior was observed in the rest of the cases. Results are presented as the inverse of the highest dilution that duplicates the value of pre-immune sera.

FIG. 9 shows the results obtained with the sera elicited against the semi-purified protein administered by intra-peritoneal route. As it is observed, the immune sera recognized the protein present in different strains, with levels similar to the one found in the strain CU385. The rest of the sera had a comparable behavior in this assay.

Example 7

Protection Induced by the Murine Sera Specific for Protein NMB1125, Against Homologous and Heterologous Strains, in the Infant Rat Model To determine the functional activity of the antisera obtained, a protection assay was conducted in the infant rat model for meningococcal infection. Twenty four rats (5-6 days old) were divided in groups of 6 rats each.

It was determined if the sera administered by intra-peritoneal route protected the rats from the infection caused by bacteria (strain CU385), inoculated by the same route one hour later. The sera of each group were pooled and diluted 1/10 (in sterile PBS) before they were inoculated in infant rats. Four hours later, the animals were sampled and viable bacteria in their blood were counted.

Figure 10:
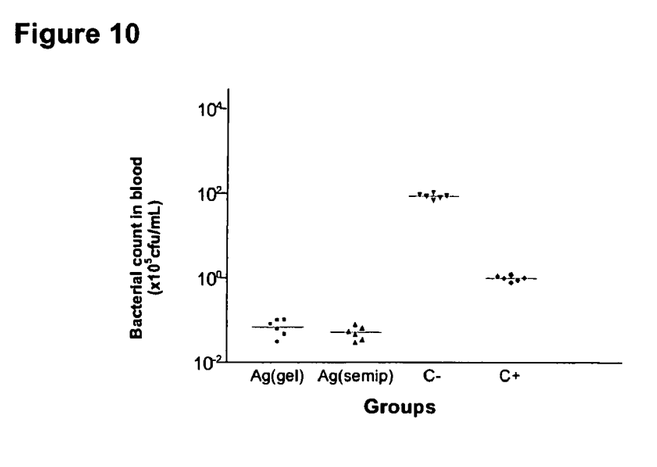
FIG. 10. Comparison among the sera elicited by immunization with the protein obtained by two methods, administered by intra-peritoneal route, in the passive protection experiments against meningococcal infection, in the infant rat model.

To interpret the results, an Analysis of Variance (Anova) was done, followed by a Dunnet's Multiple Comparison Test, where the test groups were compared with the negative control. As it is observed in FIG. 10, the groups that received antisera against the protein NMB1125 showed statistically significant differences with the negative control, and so they were considered protective in this model.

A similar assay was done infecting infant rats with strains H44/48 and 120/90, isolated from Cuban patients, which serological classification is homologous to the strain CU385. Moreover, challenge experiments were conducted with strain 233 (C:2a: P1.5) from serogroup C and strain H44/76 (B:15: P1.7,16) from serogroup B. In all cases, the antisera protected infant rats against meningococcal infection.

Example 8

Generation of Monoclonal Antibody Against Protein NMB1125 Able of Mediating the Bactericidal Activity Against *Neisseria meningitidis*

To generate monoclonal antibodies (mAbs) specific against protein NMB1125, and study the functional ability of mediating bactericidal activity against homologous and heterologous strain of *N. meningitidis*, an immunization schedule was conducted with a preparation of protein NMB1125 with purity higher than 80% (Example 3). The immunization was done in Balb/C (H-$2^d$, female, 5-6 weeks old) and 4 doses were applied as follows: On days 0, 15 and 30 of the immunization routine, 10 μg of antigen NMB1125 per mouse (total volume 100 μl), were administered by subcutaneous route, emulsified with Freund's Adjuvant; on day 50, 10 μg of antigen per mouse in Phosphate Buffered Saline (140 mM NaCl, 270 mM KCl, 1.5 mM $KH_2PO_4$, 6.5 mM $Na_2HPO_4 \times 2H_2O$, pH 7.2) were administered by intra-peritoneal route. Blood extractions were done on days 0 and 45.

Splenocytes from the animal with the highest titer, measured by an indirect ELISA using protein NMB1125 as the coating antigen (Example 3), were fused with X63 Ag8 653 mouse myeloma cells. The resulting hybridomas were isolated and screened according to standard procedures (Gavilondo J V. 1995. Anticuerpos Monoclonales: Teoría y Práctica, Elfos Scientiae, La Habana, Cuba).

Figure 11:
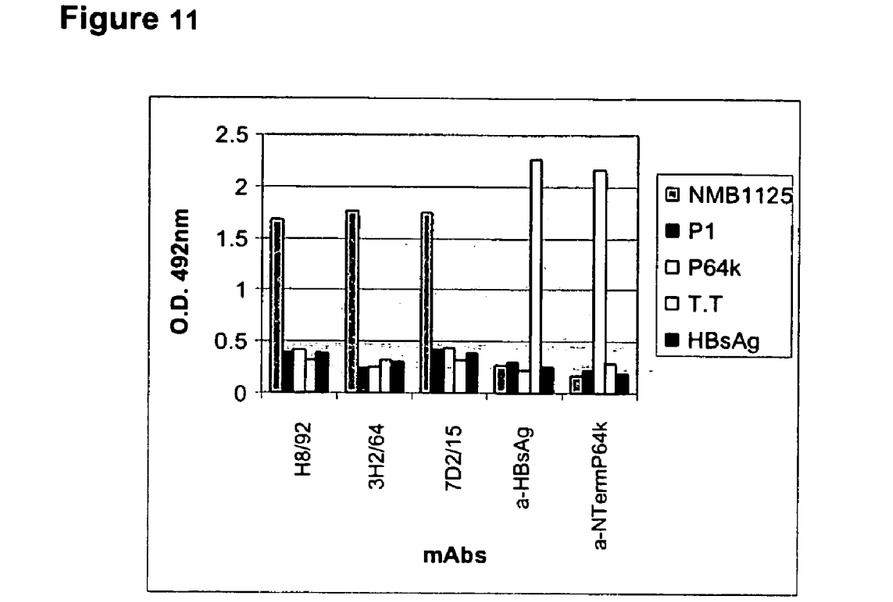
FIG. 11: Recognition of NMB1125 protein and a panel of un-related antigens by generated mAbs (mAbs H8/92, 3H2764 and 7D2/15). P1, Class 1 protein *Neisseria meningitidis* strain B:4:P1.15; P64k, E3 subunit of pyruvate dehydrogenase from *Neisseria meningitidis*; T.T, tetanus toxoid; HBsAg, Hepatitis B surface Antigen.

The reactivity of the antibodies secreted by the hybridomas directed to protein NMB1125, as well as their cross-reactivity non-related antigens, was tested by an indirect ELISA employing 5 µg/ml of each antigen, and the same concentration of each mAbs to be assayed. FIG. 11 shows the results obtained in this experiment, all together 3 positive clones were obtained (mAbs H8/92, 3H2/64 and 7D2/15) which specifically recognized protein NMB1125, and do not react neither with the amino acid sequence corresponding to the N-terminal of P64k, nor with the rest of the non-related antigens assayed.

To determine the ability of the mAbs generated against protein NMB1125 to mediate a bactericidal response against homologous and heterologous strains of Neisseria meningitidis a bactericidal test was performed. The bactericidal antibody titer was expressed as the reciprocal of the highest dilution of the antibodies tested that was able of killing 50% or more bacteria, two of the mAbs generated (3H2/64 and 7D2/15) had bactericidal titers higher than 1:128 against the homologous strain B:4:P1.19,15 and one mAb (H8/92) higher than 1:80. Moreover, they had titers higher than 1:64 against the heterologous strains B:15:P1.7,16 and C:2a:P1.5.

Example 9

Characterization of the Target Regions of the Murine Immune Response Against Protein NMB1125

In order to identify the regions in the protein, which are more frequently recognized by the murine antisera generated against the recombinant antigen a SPOTScan assay was done. A set of overlapping peptides that span the sequence of the protein was synthesized on a cellulose membrane, which was incubated with pooled sera diluted 1:100. The antigen-antibody reaction was detected by the incubation with a conjugate anti-murine immunoglobulin G-alkaline phosphatase, followed by the addition of a solution that contained the substrate Bromo-chloro-indolyl-phosphate.

Several antigenic regions common within the protein were observed, no matter the preparation that was employed for the immunization. However, in the groups immunized with the protein adjuvated with Freund's Adjuvant there was a much broader pattern of recognition.

Example 10

Recognition of the NMB1125 Protein by Human Sera

A collection of human sera, coming from convalescent individuals was employed in this study, which was performed by ELISA. The plates were coated with protein NMB1125, obtained by preparative electrophoresis (5 µg/ml). Alter blocking the plates with 3% skim milk powder in PBS containing Tween-20, the sera were diluted (1:50) in the same solution and were incubated in the plates. The immunoassay continued as it has been widely reported. Healthy donor sera were employed as negative controls. In addition, pooled sera from individuals vaccinated with a recombinant vaccine against Hepatitis B was used a non-related control (data not shown).

Figure 12:
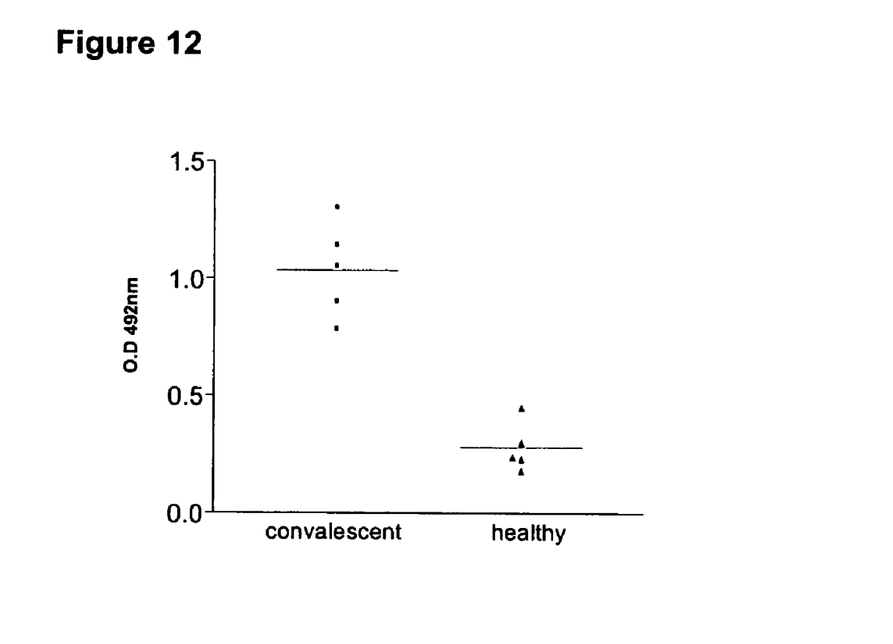
FIG. 12. Recognition of NMB1125 protein by human convalescent sera from survivors of meningococcal disease. As negative control healthy donor sera were employed. Results are shown as the absorbance (492 nm) in an ELISA type assay.

FIG. 12 shows the results obtained with 5 convalescent's sera in this assay. It can be seen that the human sera recognized the protein, which indicates that it is expressed during the meningococcal infection and it is immunogenic.

Example 11

Protein NMB1125 as a Carrier for a Peptide

Figure 13:
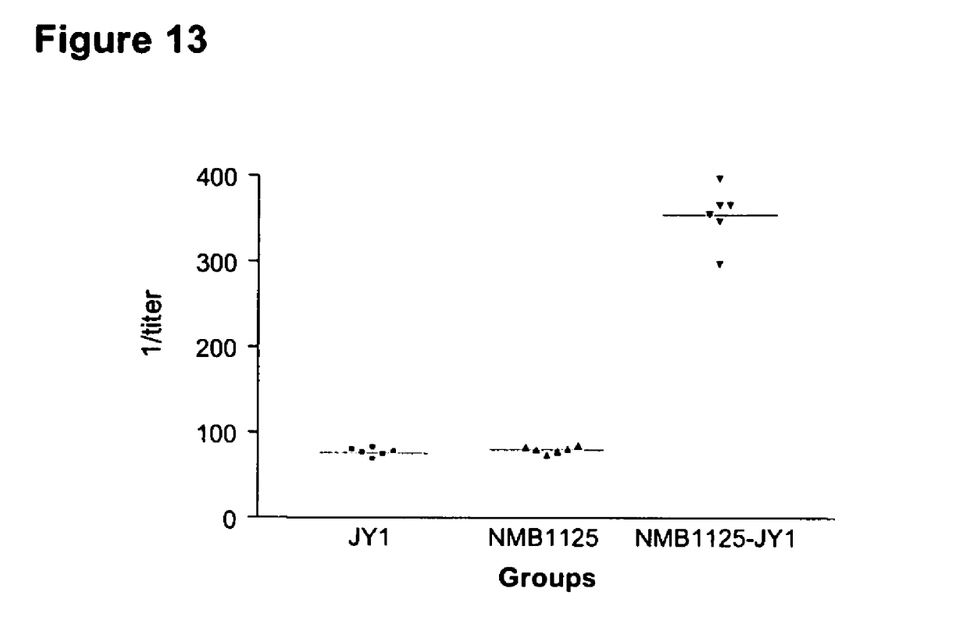
FIG. 13. JY1 anti-peptide titers from the sera of animals immunized with either free peptide (JY1), recombinant protein (NMB1125) or the conjugate JY1-NMB1125.

To demonstrate the carrier capacity of the recombinant protein NMB1125, it was conjugated to a 15 mer synthetic peptide, derived from the V3 region of protein gp120 from HIV-1, isolate JY1. The conjugation was done by the glutaraldehyde method. Free JY1 peptide, the recombinant protein NMB1125 and the conjugate JY1-NMB1125, were administered to adult mice in a 3-dose schedule, where the immunogens were emulsified with Freund's Adjuvant. Two weeks after the third dose, serum samples were obtained from the immunized animals, and the samples were analyzed by ELISA to determine the anti-peptide antibody titers. To do that, the plates were coated with free peptide (20 µg/ml) and the immunoassay continued as it has been previously described. The results of the experiment (FIG. 13) show the carrier capacity of protein NMB1125, able of significantly potentiate the antibody response against peptide JY1, after their conjugation.

The invention claimed is:

1. A method of inducing an immune response against an infection caused by *Neisseria meningitidis* in a human in need thereof, comprising administering to the human an effective amount of a pharmaceutical composition comprising a recombinant protein and a pharmaceutically acceptable carrier, said protein consisting of the amino acid sequence set forth in SEQ ID NO.: 4.

2. The method according to claim 1, wherein the pharmaceutical composition further comprises a peptide antigen.

3. The method according to claim 1, wherein the pharmaceutical composition is administered parenterally.

4. The method according to claim 1, wherein the pharmaceutical composition is administered mucosally.

* * * * *

SEQUENCE LISTING

<160> NUMBER OF SEQ ID NOS: 9

<210> SEQ ID NO 1
<211> LENGTH: 32
<212> TYPE: DNA
<213> ORGANISM: Artificial Sequence
<220> FEATURE:
<223> OTHER INFORMATION: Chemically Synthesized oligonucleotide 7738

<400> SEQUENCE: 1
ttagatctct atcccgatac cgtctatgaa gg                           32

<210> SEQ ID NO 2
<211> LENGTH: 27
<212> TYPE: DNA
<213> ORGANISM: Artificial Sequence
<220> FEATURE:

```
<223> OTHER INFORMATION: Chemically Synthesized oligonucleotide 7739

<400> SEQUENCE: 2
aagctcgagt cgtttgcctc ctttacc                                              27

<210> SEQ ID NO 3
<211> LENGTH: 262
<212> TYPE: DNA
<213> ORGANISM: Neisseria meningitidis

<400> SEQUENCE: 3
ctatcccgat accgtctatg aaggtttgaa aaacgacgac acttcgttgg gcaagcagac          60
cgaaaagatg gaaaaatact ttgtggaagc cggcaacaaa aaaatgaatg ccgccccggg         120
tgcgcacgcc atctgggact gctgctttcc gttcgggaga caaagagggc cgttccgcca         180
gtttgaagaa gagaaaaggc tgtttcccga atcgggcgta tttatggact tcctgatgaa         240
aaccggtaaa ggaggcaaac ga                                                  262

<210> SEQ ID NO 4
<211> LENGTH: 97
<212> TYPE: PRT
<213> ORGANISM: Neisseria meningitidis

<400> SEQUENCE: 4

Gln Lys Ser Leu Tyr Tyr Tyr Gly Gly Tyr Pro Asp Thr Val Tyr Glu
  1               5                  10                  15

Gly Leu Lys Asn Asp Asp Thr Ser Leu Gly Lys Gln Thr Glu Lys Met
             20                  25                  30

Glu Lys Tyr Phe Val Glu Ala Gly Asn Lys Lys Met Asn Ala Ala Pro
         35                  40                  45

Gly Ala His Ala His Leu Gly Leu Leu Leu Ser Arg Ser Gly Asp Lys
     50                  55                  60

Glu Gly Ala Phe Arg Gln Phe Glu Glu Glu Lys Arg Leu Phe Pro Glu
 65                  70                  75                  80

Ser Gly Val Phe Met Asp Phe Leu Met Lys Thr Gly Lys Gly Gly Lys
                 85                  90                  95

Arg

<210> SEQ ID NO 5
<211> LENGTH: 260
<212> TYPE: DNA
<213> ORGANISM: Neisseria meningitidis

<400> SEQUENCE: 5
ctatcccgat accgtctatg aaggtttgaa aaacgacgac acttcgttgg gcaagcagac          60
gaaaagatgg aaaaatactt tgtggaagcc ggcaacaaaa aaatgaatgc cgccccgggt        120
gcgcacgccc atctgggact gctgctttcc gttcgggaga caaagagggc gcgttccgc         180 cagtttgaag aagagaaaag gctgtttccc gaatcgggcg tatttatgga cttcctgatg        240
aaaaccggta aggaggcaa                                                     260

<210> SEQ ID NO 6
<211> LENGTH: 260
<212> TYPE: DNA
<213> ORGANISM: Neisseria meningitidis

<400> SEQUENCE: 6
ctatcccgat accgtctatg aaggtttgaa aaacgacgac acttcgttgg gcaagcagac         60
```

-continued

```
gaaaagatgg aaaaatactt tgtggaagcc ggcaacaaaa aaatgaatgc cgccccgggt    120
gcgcacgccc atctgggact gctgctttcc cgttcgggag acaaagaggg cgcgttccgc    180
cagtttgaag aagagaaaag gctgtttccc gaatcgggcg tatttatgga cttcctgatg    240
aaaaccggta aaggaggcaa                                                260

<210> SEQ ID NO 7
<211> LENGTH: 260
<212> TYPE: DNA
<213> ORGANISM: Neisseria meningitidis

<400> SEQUENCE: 7
ctatcccgat accgtctatg aaggtttgaa aaacgacgac acttcgttgg gcaagcagac     60
gaaaagatgg aaaaatactt tgtggaagcc ggcaacaaaa aaatgaatgc cgccccgggt    120
gcgcacgccc atctgggact gctgctttcc cgttcgggag acaaagaggg cgcgttccgc    180
cagtttgaag aagagaaaag gctgtttccc gaatcgggcg tatttatgga cttcctgatg    240
aaaaccggta aaggaggcaa                                                260

<210> SEQ ID NO 8
<211> LENGTH: 29
<212> TYPE: DNA
<213> ORGANISM: Artificial Sequence
<220> FEATURE:
<223> OTHER INFORMATION: Chemically Synthesized oligonucleotide 1573

<400> SEQUENCE: 8
ttccatggta gataaaagaa tggctttag                                       29

<210> SEQ ID NO 9
<211> LENGTH: 27
<212> TYPE: DNA
<213> ORGANISM: Artificial Sequence
<220> FEATURE:
<223> OTHER INFORMATION: Chemically Synthesized oligonucleotide 6795

<400> SEQUENCE: 9
aactgcaggc ttgtaaaccg ttttgtg                                         27
```